(12) United States Patent
Kessler et al.

(10) Patent No.: US 8,455,554 B2
(45) Date of Patent: Jun. 4, 2013

(54) METAL OXIDE HYDROGELS AND HYDROSOLS, THEIR PREPARATION AND USE

(75) Inventors: Vadim G. Kessler, Uppsala (SE); Gulaim A. Seisenbaeva, Uppsala (SE); Sebastian Håkansson, Alunda (SE); Maria Unell, Moheda (SE)

(73) Assignee: CaptiGel AB, Uppsala (SE)

( * ) Notice: Subject to any disclaimer, the term of this patent is extended or adjusted under 35 U.S.C. 154(b) by 658 days.

(21) Appl. No.: 12/304,513

(22) PCT Filed: Jun. 12, 2007

(86) PCT No.: PCT/SE2007/000577
§ 371 (c)(1),
(2), (4) Date: Jun. 19, 2009

(87) PCT Pub. No.: WO2007/145573
PCT Pub. Date: Dec. 21, 2007

(65) Prior Publication Data
US 2009/0297604 A1 Dec. 3, 2009

Related U.S. Application Data

(60) Provisional application No. 60/812,779, filed on Jun. 12, 2006.

(51) Int. Cl.
*A61K 9/14* (2006.01)
*B01J 13/00* (2006.01)

(52) U.S. Cl.
USPC .................................. 516/88; 424/484

(58) Field of Classification Search
USPC .................................. 516/88; 424/484
See application file for complete search history.

(56) References Cited

U.S. PATENT DOCUMENTS

| | | | |
|---|---|---|---|
| 2,453,847 A | 11/1948 | Kimberlin | |
| 4,349,456 A | 9/1982 | Sowman | |
| 5,096,745 A | 3/1992 | Anderson et al. | |
| 5,200,334 A | 4/1993 | Dunn et al. | |
| 5,958,591 A * | 9/1999 | Budd | 428/403 |
| 2006/0216513 A1 * | 9/2006 | Musick et al. | 428/404 |
| 2008/0134939 A1 | 6/2008 | Arpac et al. | |

FOREIGN PATENT DOCUMENTS

| | | |
|---|---|---|
| DE | 102004009287 A1 | 9/2005 |
| EP | 0093212 A1 | 11/1983 |
| EP | 0281034 | 9/1988 |
| EP | 1020405 | 7/2000 |
| EP | 1614694 | 1/2006 |
| JP | 06-298533 | * 10/1994 |
| JP | 6-298533 A | 10/1994 |
| WO | WO 02/06159 A1 | 1/2002 |

OTHER PUBLICATIONS

Fu et al. ("Anatase TiO2 nanolayer coating on cobalt ferrite nanoparticles for magnetic photocatalyst", Materials Letters 59 (Aug. 2005), 3530-3534).*
Watson et al. ("Synthesis of a novel magnetic photocatalyst by direct deposition of nanosized TiO2 crystals onto a magnetic core", Journal of Photochemistry and Photobiology A: Chemistry 148 (2002) 303-313).*
Sakai et al, Journal of the American Chemical Society, pp. 4944-4945 (online Mar. 23, 2006).
Khimich et al, Russian Journal of Applied Chemistry, 79(3):351-355 (Mar. 2006).
Sanchez et al, Journal of Non-Crystalline Solids, 100:65-76 (1988).
Shis et al, "Dispersion of SiC whiskers in mixtures of ethanol and ethanediol", Ceramics International, 19(4):215-217 (1993) (Abstract).
Hsing et al, "Polyethyleneimine surfactant effect on the formation of nano-sized BaTiO3 powder via a solid state reaction", Journal of Alloys and Compounds, 509(28):7632-7638 (2011) (Abstract).
Nass et al, Synthesis of an Alumina Coating from Chelated Aluminium Alkoxides, Journal of Non-Crystalline Solids, 121(a/3):329-333 (1990).

* cited by examiner

*Primary Examiner* — Ling Choi
*Assistant Examiner* — Chun-Cheng Wang
(74) *Attorney, Agent, or Firm* — Porter Wright Morris & Arthur LLP

(57) ABSTRACT

A process for preparing a hydrosol of one or more metal oxides, e.g. titanium dioxide, comprising preparing a metal alkoxide solution in a water-miscible organic solvent, e.g. an alcohol; providing an aqueous solvent; mixing the metal alkoxide solution with the aqueous solvent in a volume or weight proportion to form a single-phase aqueous sol colloid (hydrosol) of hydrated metal oxide in absence of a non-ionic block polymer surfactant. Also disclosed is a corresponding hydrogel; water-insoluble particles encapsulated in hydrated metal oxide and a process for their encapsulation; uses of the encapsulation products.

27 Claims, 4 Drawing Sheets

A

B

Solid TiO$_2$

Ti-citrate in solution

A

B

METAL OXIDE HYDROGELS AND HYDROSOLS, THEIR PREPARATION AND USE

RELATED APPLICATION

This application is a 371 of PCT/SE2007/000577 filed Jun. 12, 2007 and claims priority under 35 U.S.C. §119 of U.S. Application Ser. No. 60/812,779 filed Jun. 12, 2006.

FIELD OF THE INVENTION

The present invention relates to metal oxide hydrogels and hydrosols, methods for their preparation, and their use, in particular for encapsulation of water-insoluble particles.

BACKGROUND OF THE INVENTION

Isolating molecules of pharmaceuticals, dyes, magnetic or optically sensitive particles or plant, animal or human tissues or cells as well as living organisms including viruses, bacteria, fungi, seeds or plant or animal embryos in the capsules not permitting transport of particles or bigger molecules through their walls with the possibility of controlled release of these objects through biocompatible chemical or biochemical treatment under ambient conditions opens tremendous perspectives in such domains as drug delivery, optical or magnetic storage of information through printing, sensor techniques, bio-delivery and even protection of biological objects, for the purpose of bio-control protection and/or preservation.

The earlier developed techniques for preparation of inorganic hydrosols and hydrogels for encapsulation purposes have been considering almost exclusively preparation of a silica gel. Two major approaches have been developed: one based on hydrolysis of silicon alkoxides using acid catalyst with subsequent addition of a buffer solution, stabilizing pH in the interval 5-7 [1, 2]. Silicon alkoxides are not soluble in water or miscible with it, which requires application of a co-solvent such as alcohol (not less than 30% in the total reaction mixture) or prolonged ultrasonic treatment or other mixing procedures to assure homogenization [1]. Other possibility is provided by hydrolysis of sodium silicate in water solution by addition of a buffer solution with pH in the interval 5-7 [3, 4]. In the latter case a considerable lack of reproducibility in encapsulation has been observed, caused by the difficulty to control local pH and provide a kinetically reproducible regime in the growth of a silica polymer [5]. Both these approaches offered polymeric gels, providing retention of the molecules or organisms trapped inside, but no true encapsulation, as these objects are released in a poorly controllable way through diffusion [2, 5]. Preparation of dense silica capsules without a possibility to release encapsulates has been reported to occur in water-in-oil [6] or oil-in-water [7] emulsions on application of stabilizing surfactants. Very recently it has been shown that heteroleptic silicon precursors, alkyl-silicon alkoxides, can give capsules, when hydrolyzed in an oil-in-water emulsion [8]. The use of metal alkoxides in the same procedure as silicon alkoxides has been claimed in [9], but was the same year shown to be impossible by the works of Livage et al. [10]. According to Livage, the hydrolysis of metal alkoxides is providing polymer sols that quickly transform into gels on addition of water. The possibility to obtain hydrosols for encapsulation purposes was proposed only through obtaining oxide gels in organic solvents and their re-peptization after transfer into water [5]. The measures proposed for obtaining such secondary sols, such as addition of strong acids or heating to at least 90° C. [11], are obviously not biocompatible. Recently [12] there has been reported preparation of core-shell Ag—$TiO_2$ nanoparticles, applying hydrolysis of titanium isopropoxide solution in ethanol by a colloid solution of silver nanoparticles in water, stabilized by a surfactant CTAB (Cetylammonium bromide). Selective formation of the shell on the surface of the particles was attributed to the catalytic action of the surfactant.

It has recently been demonstrated [13] that the hydrolysis of the chemically modified zirconium and titanium alkoxides in a water-in-hydrocarbon emulsion (a system with phase separation between two solvents) occurred as a micellar self-assembly, providing thin-walled oxide shells selectively encapsulating hydrophilic molecules.

OBJECTS OF THE INVENTION

It is an object of the invention to provide a process for preparing metal oxide hydrogels and hydrosols.

It is another object of the invention to provide a process for encapsulation of water-insoluble particles in a main group metal oxide and/or a transition metal by means of a metal oxide hydrogel or hydrosol.

An additional object of the invention is to provide water-insoluble particles encapsulated in metal oxide.

Further objects of the invention comprise uses of water-insoluble particles encapsulated in metal oxide.

Still further objects of the invention will become evident from the following summary of the invention, the description of preferred embodiments thereof, and the appended claims.

SUMMARY OF THE INVENTION

If not otherwise indicated, in this application a metal oxide or alkoxide is a main group metal oxide or transition metal oxide or a mixture of such metal oxides or metal alkoxides.

According to the present invention is disclosed a process for preparing a hydrosol of one or more metal oxides, comprising:
i) Preparing a metal alkoxide solution of one or more metal alkoxides in a water-miscible organic solvent;
ii) Providing an aqueous solvent;
iii) Optionally providing an aqueous solvent having a pH of from pH 0 to pH 7;
iv) Optionally mixing measured volumes of the solution of step i) and of the aqueous solvent of step iii) to form metal oxide micelles in the water-miscible organic solvent;
v) mixing the metal alkoxide solution of step i) or the water-miscible organic solvent comprising metal oxide micelles of step iv) with the aqueous solvent of step ii) in volume or weight proportions to form a single-phase aqueous sol colloid (hydrosol) of hydrated metal oxide;
with the proviso that the hydrosol does not comprise non-ionic block polymer surfactant. Preferred embodiments of the process for preparing the hydrosol are disclosed in claims 2-8.

Also disclosed according to the invention is a hydrosol of hydrated metal oxide, in particular one obtainable by the process of the invention, which does not comprise non-ionic block polymer surfactant.

According to the present invention, a process for preparing a hydrogel of one or more metal oxides, which does not comprise non-ionic block polymer surfactant, comprises storing the aqueous hydrosol of hydrated metal oxide of the invention for a period of time sufficient to provide for sol-gel transition. From the hydrogel of hydrated metal oxide of the invention, water and/or solvent can be optionally removed at, for instance, reduced pressure to form a dried hydrogel of one or more metal oxides, which does not comprise non-ionic block polymer surfactant.

According to a preferred aspect of the invention is disclosed a process for encapsulation of water-insoluble particles in hydrated metal oxide or a mixture of hydrated metal oxides comprising:
a) Preparing a metal alkoxide solution in a water-miscible organic solvent;
b) Preparing a particle suspension in an aqueous solvent;
c) Mixing the solution of step a) and the suspension of step b) in a volume or weight proportion suitable for forming a suspension of said particles in a single-phase hydrosol of hydrated metal oxide;
or, alternatively to steps b) and c):
$b_1$) providing water or an aqueous solvent having a pH of from pH 0 to pH 7;
$c_1$) mixing measured volumes of the solution of step a) and of the water or aqueous solvent of step $b_1$ to form metal oxide micelles in the water-miscible organic solvent of step a);
$c_2$) mixing the water-miscible organic solvent comprising metal oxide micelles of step $c_1$ with an aqueous solvent to form a single-phase hydrosol of hydrated metal oxide;
$c_3$) dispersing water-insoluble particles in the single-phase hydrosol of step $c_2$ to form a suspension of the particles therein;
d) Storing the hydrosol particle suspension of step c) or $c_3$) for a period of time sufficient to provide for formation and self-assembly of metal oxide micelles on the particles so as to form shells of hydrated metal oxide on the particles, wherein the storage time can be selected to allow for transition of the aqueous sol to an aqueous gel;
e) Optionally removing water and/or solvent from the product of step d) to form aggregates of water-insoluble particles in shells of hydrated metal oxide(s);
f) Alternatively to step e), optionally separating the particles enclosed in shells of hydrated main group metal and/or transition metal oxide(s) obtained in step d) from other components;
g) Optionally removing water and solvent from the product of step f);
with the proviso that the method does not comprise the use of a non-ionic block-copolymer surfactant.

Preferred embodiments of the process are disclosed in the appended claims 15-32 and 35-39.

The initially prepared metal alkoxide in solution can be modified by addition of heteroligands such as carboxylic acids, diketones, ketoesters, polyols, or alcohols containing additional amino-, ether-, keto-aldehyde groups, or phenols, or alkanolamines. Carboxylic acids involving aromatic fragments, aminoacids and proteins with potential for drug delivery applications are particularly preferred as modifying ligands.

According to a preferred aspect of the invention the metal alkoxide solution can be subjected to hydrolysis by addition of controlled amounts of water with pH in the interval from 0 to 7, most preferred from 0 to 2, adjusted by addition of a strong acid (such as HCl, $HNO_3$, $H_2SO_4$, $HClO_4$, $CF_3SO_3H$ or $PhSO_3H$) or its solution in the same or other organic solvent miscible with that applied for dissolution of the initial metal alkoxide. The amount of added water provides the possibility for formation of oxide micelles through hydrolysis-polycondensation in an organic medium. It is preferred for the amount of water added to be from 0 to 5 molar equivalents to the amounts of metals, in particular from 0.01 to 4.0 molar eq., most preferred from 0.05 to 1.0 molar eq. All the applied organic solvents should, in the volumes proposed for further formulations, be miscible with an aqueous medium without phase separation. The suspension resulting from mixing of the organic metal alkoxide solution with the chosen aqueous medium can be left in a liquid form or dried via evaporation at ambient pressure or in vacuum or in a gas flow or through spraying of the initial suspension as well as freeze drying.

According to the invention is additionally disclosed a method of controlled release of the encapsulated particles or fragments thereof. In this method the product of the process of the invention is contacted with a pH-adjusted aqueous ligand solution, for instance a carboxylate or polycarboxylate solution, in particular a solution of citrate, lactate, succinate, oxalate, etc. It is preferred for the aqueous ligand solution to have a pH of from pH 4 to pH 9, in particular of from pH 5 to pH 7.

According to a preferred aspect of the process of the invention comprises the use of metal alkoxides and precursors of metal alkoxides, such as main group metal and/or transition metal methoxides, ethoxides, n-propoxides, iso-propoxides, n-butoxides, sec-butoxides, iso-butoxides, tert-butoxides, n-pentoxides, iso-pentoxides, sec-pentoxides, tert-pentoxides, neo-pentoxides, longer chain alcohol derivatives (with the alkyl groups containing up to 12 carbon atoms), alcohol derivatives, containing an additional donor function, such as alkoxy-, amino-, imino-, alkylamino-, alkanolamino-derivatives etc., derivatives of phenols etc., non-modified, or modified with such ligands as diketones, ketoesters, carboxylic acids, alkyls, unsaturated hydrocarbon ligands, alcohol ligands with additional donor functions, polyols, calixarenes etc., proceeds according to a micellar self-assembly mechanism, which is principally different from that the self-assembly of silica alkoxides and modified silica alkoxides, and always comprises formation of dense particles of a size and reactivity determined by self-assembly of ligands on their surface. Micelles are heterogeneous particles, which can be transferred into water for gelation and/or encapsulation if introduced into an aqueous solution by means of a water-miscible organic solvent. Moreover, if the reaction mixture is heterogeneous, the micelles will generally be concentrated on phase separation surfaces, there forming dense shells around macromolecules, particles or organisms present in the aqueous phase. Application of basic ligands, such as amines, aminoalcohols, alkanolamines, aminoacids, aminosubstituted sugars etc., in combination with acids in the preparation of the primary micelles in organic solvents provides a means of stabilizing micelles in aqueous media through electrically charged of ammonium ions (cations) on their surface and to adjust pH in the resulting hydrosol via desorption of protonating ligands forming a buffer solution. It is preferred for the buffer solution to have a pH from 4 to 10, in particular from 5 to 9, most preferred from 7.0 to 8.5, permitting to achieve a biocompatible medium. The original solution of micelles can be highly concentrated, which makes it possible to obtain final reaction mixtures with alcohol content of less than 10%. The thus obtained shells can have thick (up to 50 µm) and mechanically resistant walls in contrast to the shells obtained from metal alkoxides in water-in-hydrocarbon emulsions [13]. The specific chemical and physical properties of main group metal oxides and transition metal oxides such as magnetism, electric conductivity, optical activity etc. in combination with the properties of encapsulated objects offers a broad spectrum of applications. The high density of the walls of capsules produced from metal alkoxides enhances the retention of encapsulated objects. Chemical reactivity of (hydrated) main group metal oxides or transition metal oxides derived from metal alkoxides provides for chemically or biochemically controlled release of encapsulated particles or fragments thereof at ambient temperature via introduction of biocompatible ligands such as, for example, di- and polycarboxylates (citrate, lactate, succinate, oxalate etc.). The most important feature of the applied ligands is the presence of an acidic group, such as carboxylate, sulphonate, phosphonate and an additional group, which can be of either carboxylate, sulphonate, phosphonate or hydroxyl function in the alpha, beta, gamma or delta position to the first group (1 to 4 carbon atoms between the groups).

The product of the process may vary in form depending on, i.a., how it is recovered from the sol or gel state, and can, dependent on the application, be used as a liquid suspension (sol), a gel, a dry powder or particles encapsulated in a hard shells surrounded by amorphous metal oxide.

The process of the invention is based on the preparation of a solution of main group metal and/or transition metal alkoxide or modified alkoxide in such solvents as alcohols, alcohols with additional donor functions such as amino, alkylamino, ether, ester, keto- or aldehyde groups, ethers, esters, amines, amides, alkyl sulfoxides or alkyl phosphonates (with the principal requirement that they should be miscible with water without phase separation) with or without additional modification by such ligands as diketones, ketoesters, carboxylic acids, alkyls, unsaturated hydrocarbon ligands, alcohol ligands with additional donor functions, alkanolamines, polyols, calixarenes etc. As metal alkoxides can be used main group metal or transition metal methoxides, ethoxides, n-propoxides, iso-propoxides, n-butoxides, sec-butoxides, iso-butoxides, tert-butoxides, n-pentoxides, iso-pentoxides, sec-pentoxides, tert-pentoxides, neo-pentoxides, longer chain alcohol derivatives containing 6 to 12 carbon atoms, alcohol derivatives with additional donor functions, such as alkoxy-, amino-, imino-, alkylamino-, alkanolamino-derivatives etc., derivatives of phenols etc. As metals are meant lithium, sodium, potassium, magnesium, calcium, strontium, barium, aluminium, gallium, indium, thallium, lanthanum and lanthanides, titanium, zirconium, hafnium, vanadium, niobium, tantalum, chromium, molybdenum, tungsten, manganese, technetium, rhenium, iron, cobalt, nickel, copper, zinc, platinum group metals, silver and gold, tin, lead and bismuth and the mixtures of those, including heterometallic complexes involving these metals. Derivatives of aluminium, titanium, zirconium, niobium and molybdenum are particularly interesting for biological applications.

Partial hydrolysis-polycondensation of these solutions is carried out via addition of water in pure form or in a solution of a water-miscible solvent, in particular of one of the aforementioned organic solvents. It is preferred for the water to be of neutral pH or of a pH from 0 to 7, in particular from 0 to 2, adjusted by addition of a strong acid.

The obtained organic metal alkoxide solution is mixed with water or an aqueous solution in which the particles for encapsulation are dispersed. The aqueous solution may contain a water-miscible organic solvent and/or one or more inorganic or organic salts (such as $MX_n$, $R_4NX$, where M=Li, Na, K, Rb, Cs, Mg, Ca, Sr, Ba, or rare earth element, R=$CH_3$, $C_2H_5$, $C_3H_7$, $C_4H_9$; X=F, Cl, Br, I, OH, $NO_3^-$, $½SO_4^{2-}$, $ClO_4^-$, $CN^-$, $SCN^-$, etc.). Such salts are believed to enhance self-assembly and to decrease the retention of water in the shells, which is useful for the preparation of mechanically stable, crack-free shells. Mixing of the metal alkoxide solution with the aqueous particle suspension produces a hydrosol that self-assembles around particles, providing dense shells with modifying ligands assembled on their surface. The process does not require the application of separate surfactants (such as block-copolymers of polyesters or polyethers/polyalcohols) or catalysts. In order to protect the objects for encapsulation a protective/inert atmosphere can be applied, for example, an oxygen-free atmosphere. To decelerate the self-assembly of the colloid solutions obtained by mixing of the metal alkoxide solution and the initial suspension it is preferred to use cooling to a temperature of from −75° C. to +15° C., in particular from −45° C. to +10° C., most preferred from −20° C. to 0° C. To accelerate the self-assembly of the colloid solutions obtained by mixing of the alkoxide solution and the initial suspension it is preferred to use heating from +25° C. to +145° C., in particular from +30° C. to +130° C., most preferred from +50° C. to +120° C. Homogeneity of the metal alkoxide solution and/or the sol or gel colloid can be improved by ultrasonic treatment. Encapsulation of the water-insoluble particles (molecules, tissues, cells or organisms, etc., occurs within a time varying from a few seconds, in particular of from 1 to 20 seconds, and up to several hours, for instance two, three or six hours. It is preferred for the encapsulation time to be from 5 seconds to 6 hours, in particular from 5 s to 1 h, most preferred from 10 s to 30 min. The obtained capsules can be left in solution as a suspension or be separated by drying. The latter, dependent on application, can be realized as ambient pressure drying, vacuum drying, freeze drying, drying under flow of a gas or spray-drying. They can be purposely separated from any admixture of the non-entrapped components by repeated washing with solvents with or without filtration. Drying of the colloids can be used for better preservation of the encapsulated material. Drying at low temperatures or freeze-drying can be used for the unaltered preservation of biological matter encapsulated in metal oxide shells.

The obtained encapsulates can be stored at different conditions. They can, if desired, be dissolved almost immediately by addition of aqueous solutions of biocompatible ligands comprising weak acidic functions, preferably in a concentration of from 0.01 to 5.0 M, in particular of from 0.01 to 2 M, most preferred of from 0.05 to 1.0 M. Preferred biocompatible ligands are carboxylate or polycarboxylate ligands, but also aminocarboxylate or hydroxyl-carboxylate ligands. The dissolution process is associated with the release of the originally applied modifying ligands that can thus be controllably delivered into the solution through this procedure. Macrocapsules of a size of from several micrometers and to up to 3 mm can also be opened by physical treatment, such as mechanic, ultrasound or light (laser) treatment.

The invention will now be explained in greater detail by reference to a number of preferred but not limiting embodiments.

DESCRIPTION OF A PREFERRED EMBODIMENT OF THE INVENTION

Figure 1:
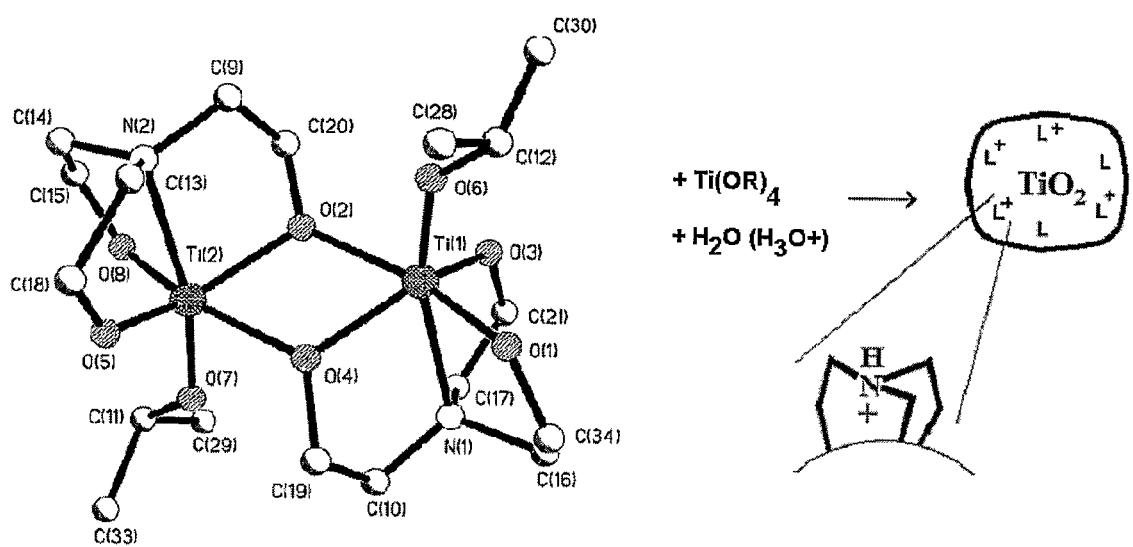
FIG. 1 is a rough scheme illustrating the self-assembly of preformed micelles (A) around (micro-) heterogeneous objects in aqueous solution (B)
Figure 1:
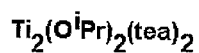
Figure 1:
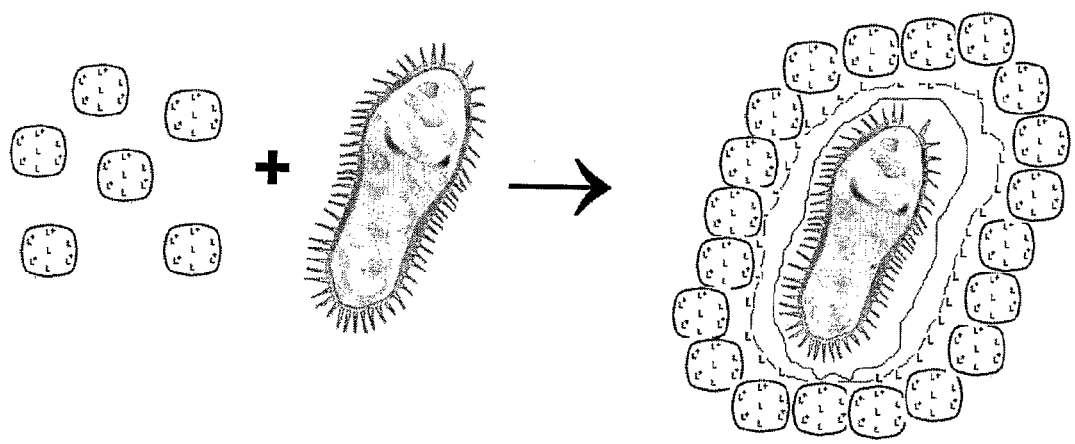
Figure 2:
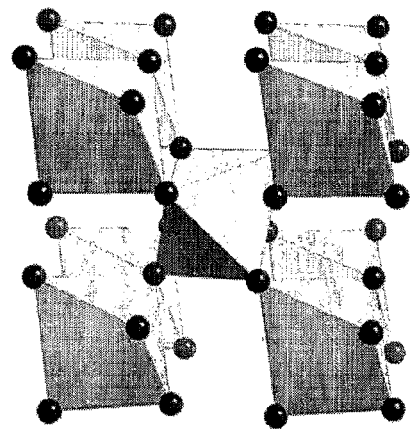
FIG. 2 shows the release of encapsulated material (A) through dissolution of the metal oxide shells by means of biocompatible ligands (B)
Figure 2:
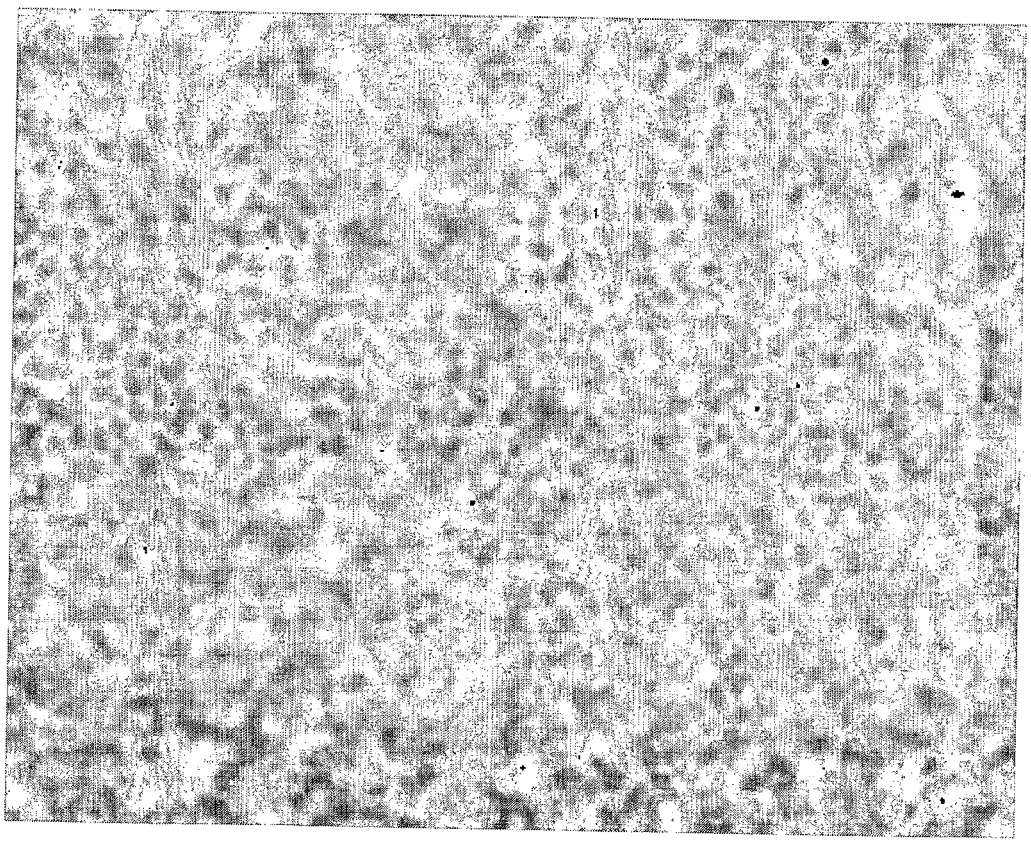
Figure 2:
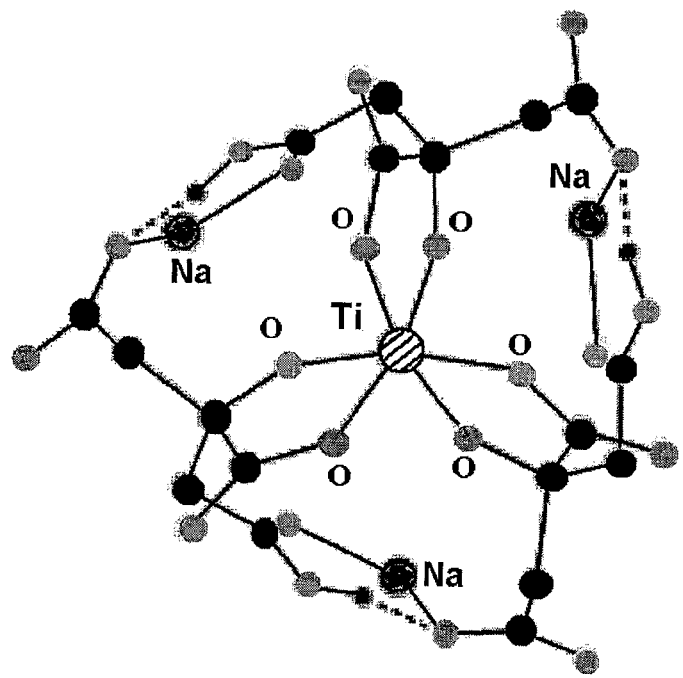
Figure 2:
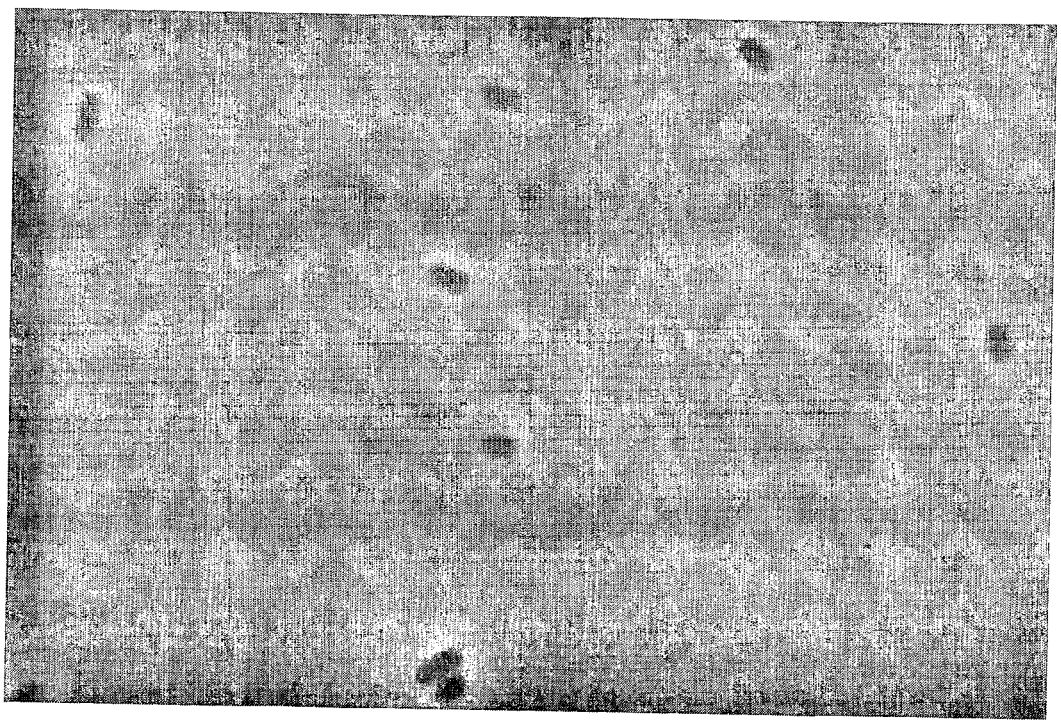
Figure 3:
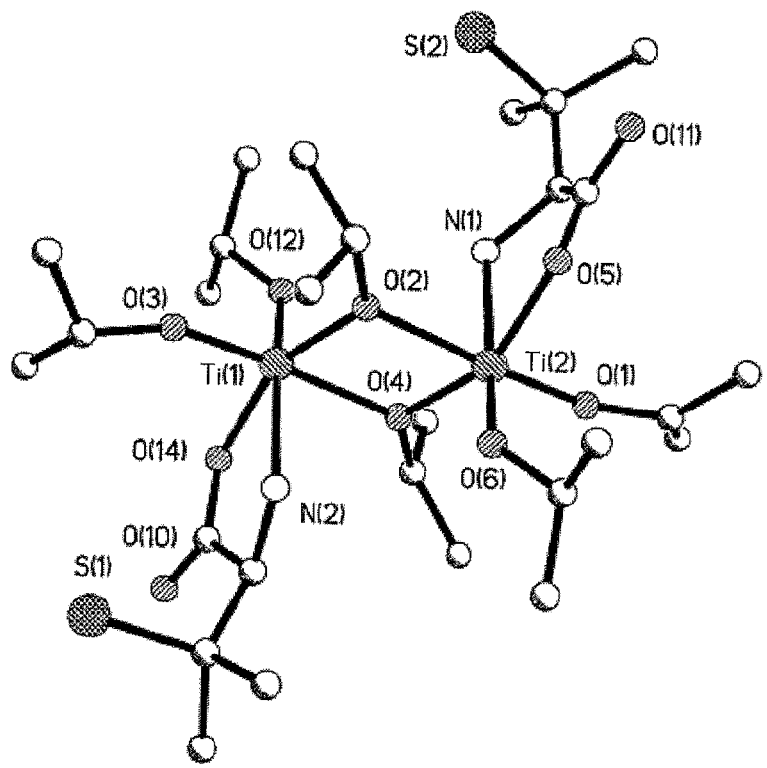
FIG. 3 shows the molecular structure of titanium alkoxide precursor species modified by penicillamine, titanium isopropoxide (A), and titanium n-propoxide (B).
Figure 3:
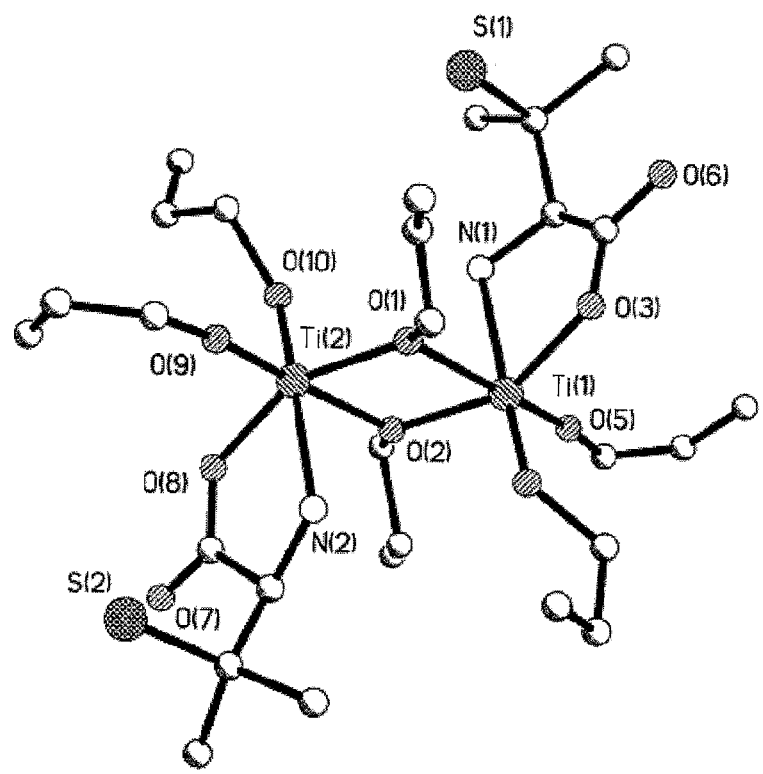

All chemicals were purchased from Aldrich and used as received.

Example 1

Encapsulation of 2.2 μm Polystyrene Beads in Hydrated Oxide Shells Obtained from Chemically Modified and Pre-Hydrolysed Precursor Initial precursor solution was obtained by dissolving 2 mL Ti(O"Pr)$_4$ in 8 mL anhydrous "PrOH and subsequently adding 0.5 mL triethanolamine. Then 1 mL of hydrolyzing solution, prepared by mixing 0.4 mL 0.1 M HNO$_3$ with 1.6 mL "PrOH, was added on stirring to the modified precursor solution, providing an organic sol. 1 mL of the sol was quickly added by means of a syringe to 5 mL of suspension of microbeads (Duke Scientific Corp., Palo Alto, Calif., USA) in water stirred by a magnetic stirrer in a glass flask. The resulting slightly opaque hydrosol was poured into a Petri dish to produce a slightly opaque gel within about 30 min. The gel was then washed with water several times and dried in the open for 1 h. Optical microscopy showed that the spheres were covered by a shell of hydrated oxide (with 100-250 nm wall thickness), and further incorporated into gel aggregates measuring from tenths of micrometers to about 1 mm. Covering particles, possessing specific optical properties (reflection and/or absorption) with a transparent gel layer is of special interest in solar control applications.

Example 2

Encapsulation of *Arthrobacter chlorophenolicus* A6G in Hydrated Oxide Shells Obtained from Chemically Modified and Pre-Hydrolysed Precursor Pre-prepared organic sol obtained according to Example 1 (1 mL) was added to 10 mL of suspension of bacteria *Arthrobacter chlorophenolicus* A6G in aqueous isotonic sodium chloride solution. The obtained slightly opaque hydrosol was poured into a Petri dish and was converted into a slightly opaque monolithic gel within 30 min. The gel was then washed several times with isotonic aqueous NaCl solution. Optical microscopy showed that the applied microorganisms were covered by a shell of hydrated oxide (with 100-250 nm wall thickness), and further incorporated into gel aggregates measuring from tenths of micrometers to about 1 mm.

Example 3

Liberation of the Encapsulated Bacteria and Subsequent Viability Tests

The gel encapsulate of *Arthrobacter chlorophenolicus* A6G (about 1 g) obtained and characterized as in Example 2 was added to a citrate buffer solution with pH=6.00 and total concentration 0.10 M (10 mL). Complete dissolution with formation of a transparent suspension of bacteria in the prepared mixture of solvents was achieved within 5 min on gentle stirring. The obtained solution was spread on cultivation plates revealing the possibility to obtain densities of the surviving microorganisms to up to $5 \cdot 10^5$ cfu/mL, corresponding to a survival rate of 0.25%.

Example 4

Improvement of the Biocompatibility of Encapsulating Material Through Ligand Choice Initial precursor solution was obtained by dissolving 4 mL Ti(OEt)$_4$ in 6 mL anhydrous EtOH and adding 1.0 mL triethanolamine. Then 1 mL of hydrolyzing solution, prepared by mixing 0.5 mL 0.5 M HNO$_3$ with 2.0 mL EtOH, was added providing an organic sol. 1 mL of the sol was quickly added by means of a syringe to 9 mL of a suspension of *Arthrobacter chlorophenolicus* A6G in aqueous isotonic sodium chloride solution. The obtained slightly opaque hydrosol was poured into a Petri dish and was converted into a slightly opaque monolithic gel within 30 min. The gel was then washed several times with isotonic aqueous NaCl solution. Optical microscopy showed that the applied microorganisms were covered by a shell of hydrated oxide (with 100-250 nm wall thickness), and further incorporated into gel aggregates measuring from tenths of micrometers to about 1 mm. Liberation of encapsulated organisms according to Example 3 with subsequent viability test revealed a survival rate of 6%.

Example 5

Tests of Biocompatibility of Hydrosol Encapsulation for Different Microorganisms Initial precursor solution was obtained by dissolving 5 mL Ti(OEt)$_4$ in 5 mL anhydrous EtOH and adding 1.5 mL triethanolamine. Then 1.0 mL of hydrolyzing solution, prepared by mixing 0.5 mL 0.5 M HNO$_3$ with 2.0 mL EtOH, was added providing an organic sol. 1 mL of the sol was quickly added by means of a syringe to 9 mL of a suspension containing either the bacteria *Lactobacillus plantarum* or the yeast *Pichia anomala* in isotonic aqueous NaCl solution. The obtained slightly opaque hydrosol was poured into a Petri dish and was converted into a slightly opaque monolithic gel within 30 min. The gel was then washed several times with isotonic aqueous NaCl solution. Optical microscopy showed that the applied microorganisms were covered by a shell of hydrated oxide (with 100-250 nm wall thickness), and further incorporated into gel aggregates measuring from tenths of micrometers to about 1 mm. Liberation of encapsulated organisms according to Example 3 with subsequent viability test revealed survival rates of 73% of the *L. plantarum* and 100% of *P. anomala*.

Example 6

Encapsulation of the Seeds of *Arabidopsis* in Hydrated Oxide Shells Obtained from Chemically Modified and Pre-Hydrolysed Precursor Initial precursor solution was obtained by dissolving 4 mL Ti(O"Pr)$_4$ in 6 mL anhydrous "PrOH and adding 2 mL triethanolamine. Then 2.5 mL of hydrolyzing solution, prepared by mixing 0.5 mL 0.1 M HNO$_3$ with 2.0 mL "PrOH, was added to form an organic sol. 1 mL of the organic sol was quickly added by means of a syringe to 10 mL suspension of 0.05 g of *Arabidopsis* seeds in 8 mL distilled water. The obtained slightly opaque hydrosol was poured into a Petri dish and dried in the open for 1 h. The seeds were covered with a shells having wall thickness of about 1 μm by Scanning Electron Microscopy (SEM) observation. The shells were not uniform, containing cracks with the depth of 0.5-0.8 μm, formed apparently through shrinkage on drying.

Example 7

Encapsulation of the Seeds of *Arabidopsis* in Hydrated Oxide Shells Obtained from Chemically Modified and Pre-Hydrolysed Precursor and Applying a Salt Solution to Avoid Shrinkage Initial precursor solution was obtained by dissolving 4 mL Ti(O"Pr)$_4$ in 6 mL anhydrous "PrOH and adding 2 mL triethanolamine. Then 2.5 mL of hydrolyzing solution, prepared by mixing 0.5 mL 0.1 M $HNO_3$ with 2.0 mL ″PrOH, was added to form an organic sol. 1 mL of the organic sol was quickly added by syringe to 10 mL of suspension of 0.05 g of *Arabidopsis* seeds in 8 mL isotonic NaCl solution. The obtained slightly opaque hydrosol was poured out in a Petri dish and dried in a flow of dry air for 1 h. The seeds were covered with uniform crack-free shells with wall thickness of about 1 μm by SEM observation.

Example 8

Application of Anti-Inflammatory Drugs as Co-Modifying Ligands

Initial precursor sol was obtained by dissolving 2 mL Ti(O″Pr)$_4$ in 8 mL anhydrous ″PrOH and adding 0.9 mL triethanolamine and 0.1 g ibuprofen or 0.1 g penicillamine, respectively. Then 1.0 mL of hydrolyzing solution, prepared by mixing 0.5 mL 0.1 M $HNO_3$ with 2.0 mL ″PrOH, was added to form an organic sol. 1 mL of the organic sol was added to 1 mL of granulated mesoporous $Al_2O_3$ in 4 mL water. The hydrosol and then hydrogel was formed on constant shaking of the mixture, which was then dried in the open. The granulae were covered with shells with thickness about 1 μm. Transfer of the coated granulae into water again does not lead to considerable immediate release of ibuprofen according to UV-measurements. Ibuprofen is released quantitatively on treatment by citrate buffer with pH=6.0. UV-measurements of the application with penicillamine as co-modifying ligand indicates that the penicillamine residue is, in the absence of polycarboxylate ligands, conserved in the gel shell with the same coordination arrangement around the metal atom as in the initial modified alkoxide.

Example 9

Preparation of Iron Oxide Hydrosol and its Application for Encapsulation of Indium Tin Oxide Nanoparticles Initial precursor sol was obtained by dissolving 0.4 g iron ethoxide, $Fe_5O(OEt)_{13}$, in 4 mL anhydrous ethanol and then adding, on vigorous stirring, 1 mL of a solution prepared by mixing 0.5 mL 0.1 M $HNO_3$ with 5 mL EtOH. 2 mL of the thus obtained dark reddish orange sol was added to 8 mL of distilled water. The obtained hydrosol is stable for several days at room temperature. Nanoparticles of indium tin oxide (30 nm in diameter, provided by MG-Consulting, Italy), 0.05 g, were dispersed in the obtained hydrosol by a short ultrasonic treatment (0.14 kW bath, 3 min). The suspension was poured into a Petri dish and dried in the open. The product consist of aggregates of particles covered by oxide shells with thickness of about 50-70 nm by SEM observations. Deposition of such particles on glasses provides an approach to solar control applications.

Example 10

Preparation of Transparent Hydrosol of Molybdenum Trioxide Monohydrate from Molybdenum Alkoxide, Derived from an Alcohol Possessing Additional Donor Function Molybdenum dioxo-2-methoxyethoxide, $MoO_2(OC_2H_4OCH_3)_2$, —a derivative of 2-methoxyethanol, an etheroalkoxide, 0.21 g, was dissolved in 3 mL of the parent alcohol, $HOC_2H_4OCH_3$. The solution was poured out into 5 mL of distilled water. The clear light blue sol remained uniform and transparent during 1 week. Drying of the sol in vacuum (0.1 mm Hg) resulted in light blue powder identified as $MoO_3.H_2O$ by powder X-ray. The sol possessed photochromic properties: it turned intensively blue when exposed to the sunlight and turned again colourless after storage in darkness for 0.5-2 h. Deposition of such sol on glasses provides an approach to photochromic applications.

REFERENCES

1. Zink J. I., Nishido F., Yamanaka S., Nishida C., Ellerby L., Dunn B. S., Valentine J. S., International Patent WO 93/04196, 4 Mar. 1993; Avnir D., Braun S., Lev O., Ottolenghi M., Chem. Mater., 1994, 6, 1605.
2. Barbé C., Bartlett J., Kong L., Finnie K., Lin H. Q., Larkin M., Calleja S., Bush A., Calleja G., Adv. Mater., 2004, 16, 1959.
3. Bhatia R. B., Brinker C. J., Gupta A. K., Singh A. K., Chem. Mater., 2000, 12, 2434.
4. Coiffier A., Coradin T., Roux C., Bouvet O. M. M., Livage J., J. Mater. Chem., 2001, 11, 2039.
5. Livage J., Coradin T., Encapsulation of Enzymes, Antibodies and Bacteria in the Handbook of Sol-Gel Science and Technology, Vol. 1, P. 485.
6. Schuleit M., Luisi P. L., Biotechnol. Bioeng., 2001, 72, 249.
7. Magdassi S., Avnir D., Seri-Levy A., Lapidot N., Sorek Y., Gans O., International Patent WO 00/09652, 24 Feb. 2000.
8. Ahn B. Y., Seok S. I., Baek I. C., Hong S. I., Chem. Commun., 2006, 189.
9. Yamamoto T., European patent application 88102921.9, Date of filing 26 Feb. 1988.
10. Sanchez C., Livage J., Henry M., J. Non-Cryst. Solids, 1988, 100, 65.
11. Liu Z., Deng J., Li D., Anal. Chim. Acta, 2000, 407, 87.
12. Sakai H., Kanda T., Shibata H., Ohkubo H., Abe M., J. Amer. Chem. Soc., 2006, 128, 4945.
13. Spijksma G., Licentiate Thesis, SLU, Sweden, 2005.

The invention claimed is:
1. A process for encapsulation of water-insoluble particles in a hydrated metal oxide or a mixture of hydrated metal oxides, comprising:
 a) preparing a metal alkoxide solution of one or several metal alkoxides in an alcohol which is miscible with water without phase separation;
 b) preparing a particle suspension in an aqueous solvent having a pH of from pH 0 to pH 7;
 c) mixing the solution of step a) and the suspension of step b) in a volume or weight proportion suitable for forming a suspension of said particles in a single-phase aqueous sol colloid of hydrated metal oxide(s); and
 d) storing said aqueous sol colloid particle suspension for a period of time sufficient to provide for formation and self-assembly of micelles of metal oxide(s) on the particles so as to form shells of hydrated metal oxide(s) on the particles, wherein the storage time can be selected to allow for transition of the aqueous sol to an aqueous gel;
 e) optionally removing water and/or solvent from the product of step d) to form aggregates of water-insoluble particles in shells of hydrated metal oxide(s);
 f) alternatively to step e), optionally separating the particles enclosed in shells of hydrated metal oxide(s) obtained in step d) from other components; and
 g) optionally removing water and alcohol from the product of step f);

with the proviso that the process does not comprise the use of a surfactant.

2. The process of claim 1, wherein the particles comprise live or dead single- or multiple-cell organisms or organelles, plant, animal or human tissue or cells or extracts thereof, or non-biological macromolecules or particles.

3. The process of claim 1, wherein the metal alkoxide is a methoxide, ethoxide, n-propoxide, isopropoxide, n-butoxide, or amyloxide.

4. The process of claim 1, wherein the metal oxide is selected from the group consisting of magnesium oxide, aluminum oxide, titanium oxide, zirconium oxide, niobium oxide, and molybdenum oxide.

5. A process for encapsulation of water-insoluble particles in a hydrated metal oxide or a mixture of hydrated metal oxides, comprising:
   a) preparing a metal alkoxide solution of one or several metal alkoxides in an alcohol which is miscible with water without phase separation, wherein at least one of the one or more metal alkoxides comprises at least one ligand other than alkoxide;
   b) preparing a particle suspension in an aqueous solvent having a pH of from pH 0 to pH 7;
   c) mixing the solution of step a) and the suspension of step b) in a volume or weight proportion suitable for forming a suspension of said particles in a single-phase aqueous sol colloid of hydrated metal oxide(s); and
   d) storing said aqueous sol colloid particle suspension for a period of time sufficient to provide for formation and self-assembly of micelles of metal oxide(s) on the particles so as to form shells of hydrated metal oxide(s) on the particles, wherein the storage time can be selected to allow for transition of the aqueous sol to an aqueous gel;
   e) optionally removing water and/or solvent from the product of step d) to form aggregates of water-insoluble particles in shells of hydrated metal oxide(s);
   f) alternatively to step e), optionally separating the particles enclosed in shells of hydrated metal oxide(s) obtained in step d) from other components; and
   g) optionally removing water and alcohol from the product of step f);
with the proviso that the process does not comprise the use of a surfactant.

6. A process for encapsulation of water-insoluble particles in a hydrated metal oxide or a mixture of hydrated metal oxides, comprising:
   a) preparing a metal alkoxide solution of one or several metal alkoxides in an alcohol which is miscible with water without phase separation, wherein at least one of the one or more metal alkoxides comprises at least one ligand other than alkoxide, wherein, at the least, one ligand other than alkoxide is a carboxylate, beta-diketonate, ketoesterate, diolate, polyolate, or carbohydrate;
   b) preparing a particle suspension in an aqueous solvent having a pH of from pH 0 to pH 7;
   c) mixing the solution of step a) and the suspension of step b) in a volume or weight proportion suitable for forming a suspension of said particles in a single-phase aqueous sol colloid of hydrated metal oxide(s); and
   d) storing said aqueous sol colloid particle suspension for a period of time sufficient to provide for formation and self-assembly of micelles of metal oxide(s) on the particles so as to form shells of hydrated metal oxide(s) on the particles, wherein the storage time can be selected to allow for transition of the aqueous sol to an aqueous gel;
   e) optionally removing water and/or solvent from the product of step d) to form aggregates of water-insoluble particles in shells of hydrated metal oxide(s);
   f) alternatively to step e), optionally separating the particles enclosed in shells of hydrated metal oxide(s) obtained in step d) from other components; and
   g) optionally removing water and alcohol from the product of step f);
with the proviso that the process does not comprise the use of a surfactant.

7. The process of claim 5, wherein the ligand other than alkoxide comprises an electron-donating group.

8. A process for encapsulation of water-insoluble particles in a hydrated metal oxide or a mixture of hydrated metal oxides, comprising:
   a) preparing a metal alkoxide solution of one or several metal alkoxides in an alcohol which is miscible with water without phase separation, wherein at least one of the one or more metal alkoxides comprises at least one ligand other than alkoxide, wherein the ligand other than alkoxide comprises an electron-donating group is selected from the group consisting of alkoxy, amino, imino, alkylamino, and alkanolamino groups;
   b) preparing a particle suspension in an aqueous solvent having a pH of from pH 0 to pH 7;
   c) mixing the solution of step a) and the suspension of step b) in a volume or weight proportion suitable for forming a suspension of said particles in a single-phase aqueous sol colloid of hydrated metal oxide(s); and
   d) storing said aqueous sol colloid particle suspension for a period of time sufficient to provide for formation and self-assembly of micelles of metal oxide(s) on the particles so as to form shells of hydrated metal oxide(s) on the particles, wherein the storage time can be selected to allow for transition of the aqueous sol to an aqueous gel;
   e) optionally removing water and/or solvent from the product of step d) to form aggregates of water-insoluble particles in shells of hydrated metal oxide(s);
   f) alternatively to step e), optionally separating the particles enclosed in shells of hydrated metal oxide(s) obtained in step d) from other components; and
   g) optionally removing water and alcohol from the product of step f);
with the proviso that the process does not comprise the use of a surfactant.

9. The process of claim 7, wherein the electron-donating ligand is selected from the group consisting of pharmaceutical agents, food additives, anti-oxidants, humidifiers, vitamins, hormones, insecticides, herbicides, anti-protozoic drugs, fungicides, bactericides, enzymes, and antibodies.

10. A process for encapsulation of water-insoluble particles in a hydrated metal oxide or a mixture of hydrated metal oxides, comprising:
   a) preparing a metal alkoxide solution of one or several metal alkoxides in an alcohol which is miscible with water without phase separation;
   b) preparing a particle suspension in an aqueous solvent having a pH of from pH 0 to pH 7;
   c) mixing the solution of step a) and the suspension of step b) in a volume or weight proportion suitable for forming a suspension of said particles in a single-phase aqueous sol colloid of hydrated metal oxide(s), wherein water is added to the metal alkoxide solution of step a) prior to mixing the solution in step c) with the aqueous particle suspension of step b) to provide for formation of main group metal and/or transition metal oxide micelles; and d) storing said aqueous sol colloid particle suspension for a period of time sufficient to provide for formation and self-assembly of micelles of metal oxide(s) on the particles so as to form shells of hydrated metal oxide(s) on the particles, wherein the storage time can be selected to allow for transition of the aqueous sol to an aqueous gel;

e) optionally removing water and/or solvent from the product of step d) to form aggregates of water-insoluble particles in shells of hydrated metal oxide(s);

f) alternatively to step e), optionally separating the particles enclosed in shells of hydrated metal oxide(s) obtained in step d) from other components; and g) optionally removing water and alcohol from the product of step f);

wherein the process does not comprise the use of a surfactant.

11. The process of claim 10, wherein the water which is added to the metal alkoxide solution of step a) prior to mixing the solution in step c) with the aqueous particle suspension of step b) is added in an amount of up to 10 molar equivalents of total metal alkoxide.

12. The process of claim 10, wherein water is added in an amount of from 0.01 to 4.0 equivalents.

13. The process of claim 10, wherein water is added in an amount of from 0.05 to 1.0 equivalents.

14. The process of claim 10, wherein the water for addition is comprised by an alcohol miscible with water without phase separation.

15. The process of claim 10, where the pH of the water for addition is adjusted by acid or buffer to a pH of from pH 0 to pH 7.

16. The process of claim 10, wherein adjustment is to pH 0 to pH 2.

17. A process for encapsulation of water-insoluble particles in a hydrated metal oxide or a mixture of hydrated metal oxides, comprising:

a) preparing a metal alkoxide solution of one or several metal alkoxides in an alcohol which is miscible with water without phase separation;

b) preparing a particle suspension in an aqueous solvent having a pH of from pH 0 to pH 7;

c) mixing the solution of step a) and the suspension of step b) in a volume or weight proportion suitable for forming a suspension of said particles in a single-phase aqueous sol colloid of hydrated metal oxide(s), wherein the solution of step a) and/or the suspension of step b) is cooled and/or heated prior to the mixing; and d) storing said aqueous sol colloid particle suspension for a period of time sufficient to provide for formation and self-assembly of micelles of metal oxide(s) on the particles so as to form shells of hydrated metal oxide(s) on the particles, wherein the storage time can be selected to allow for transition of the aqueous sol to an aqueous gel;

e) optionally removing water and/or solvent from the product of step d) to form aggregates of water-insoluble particles in shells of hydrated metal oxide(s);

f) alternatively to step e), optionally separating the particles enclosed in shells of hydrated metal oxide(s) obtained in step d) from other components; and g) optionally removing water and alcohol from the product of step f);

wherein the process does not comprise the use of a surfactant.

18. The process of claim 1, wherein the solution of step a) and/or the suspension of step b) is subjected to ultrasonic treatment prior to mixing.

19. The process of claim 1, wherein the product of step d) is dried by evaporation, sublimation, solvent exchange, and/or supercritical or freeze drying.

20. The process of claim 19, wherein the product of step e) is washed with water or an aqueous solvent.

21. The process of claim 19, wherein the dried product is subjected to heating and/or cooling.

22. A process for encapsulation of water-insoluble particles in a hydrated metal oxide or a mixture of hydrated metal oxides, comprising:

a) preparing a metal alkoxide solution of one or several metal alkoxides in an alcohol which is miscible with water without phase separation;

b) preparing a particle suspension in an aqueous solvent having a pH of from pH 0 to pH 7;

c) mixing the solution of step a) and the suspension of step b) in a volume or weight proportion suitable for forming a suspension of said particles in a single-phase aqueous sol colloid of hydrated metal oxide(s); and d) storing said aqueous sol colloid particle suspension for a period of time sufficient to provide for formation and self-assembly of micelles of metal oxide(s) on the particles so as to form shells of hydrated metal oxide(s) on the particles, wherein the storage time can be selected to allow for transition of the aqueous sol to an aqueous gel;

e) optionally removing water and/or solvent from the product of step d) to form aggregates of water-insoluble particles in shells of hydrated metal oxide(s);

f) alternatively to step e), optionally separating the particles enclosed in shells of hydrated metal oxide(s) obtained in step d) from other components; and g) optionally removing water and alcohol from the product of step f);

wherein the process does not comprise the use of a surfactant and wherein step e) or steps f) and g) are performed and the resulting dried product is subjected to mechanical fragmentation.

23. The process of claim 1, wherein the product of step f) is dried by evaporation, in a flow of a gas, by solvent exchange, and/or by supercritical or freeze drying.

24. The process of claim 1, wherein the metal alkoxide solution of step (a) is anhydrous.

25. The process of claim 10, wherein the metal alkoxide solution of step (a) is anhydrous.

26. The process of claim 17, wherein the metal alkoxide solution of step (a) is anhydrous.

27. The process of claim 22, wherein the metal alkoxide solution of step (a) is anhydrous.

* * * * *